United States Patent [19]

Küffner et al.

[11] 4,183,752
[45] Jan. 15, 1980

[54] LIGHT-SENSITIVE PHOTOGRAPHIC MATERIAL

[75] Inventors: Karl Küffner, Unterhaching; Wolfgang Lässig; Ernst Meier, both of Munich; Erwin Ranz, Leverkusen; Karl-Wilhelm Schranz, Odenthal, all of Fed. Rep. of Germany

[73] Assignee: Agfa-Gevaert Aktiengesellschaft, Fed. Rep. of Germany

[21] Appl. No.: 878,238

[22] Filed: Feb. 16, 1978

[30] Foreign Application Priority Data

Feb. 21, 1977 [DE] Fed. Rep. of Germany ....... 2707489

[51] Int. Cl.² .......................... G03C 5/30; G03C 1/06
[52] U.S. Cl. .................................... 430/382; 430/544; 430/957
[58] Field of Search ................ 96/66.3, 95, 100, 22.55

[56] References Cited

U.S. PATENT DOCUMENTS

| | | | |
|---|---|---|---|
| 4,052,213 | 10/1977 | Credner et al. | 96/66.3 |
| 4,088,491 | 5/1978 | Odenwalder | 96/66.3 |

*Primary Examiner*—Mary F. Kelley

*Attorney, Agent, or Firm*—Connolly & Hutz

[57] ABSTRACT

Development inhibitor releasing compounds are thioether compounds capable of releasing on reaction with color developer oxidation products, a diffusible mercaptan that inhibits further development of silver halide. Useful DIR compounds correspond to the formula

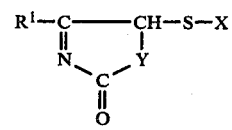

$R^1$ represents hydrocarbyl Y represents —S— or —$NR^2$—

$R^2$ represents hydrogen, hydrocarbyl or an electron-attracting substituent.

X in its preferred embodiment represents a heteroaromatic group that when split of together with the sulfur atoms forms a silver halide development inhibiting mercaptane.

8 Claims, No Drawings

LIGHT-SENSITIVE PHOTOGRAPHIC MATERIAL

This invention relates to a photographic material which contains compounds capable of releasing silver halide development inhibiting substances on reaction with oxidation products of colour developer substances.

It is known to incorporate in photographic materials compounds which react with colour developer oxidation products to release silver halide development inhibitors. Such compounds include, for example, the so-called DIR couplers (DIR=Development—Inhibitor—Releasing) which have been described in U.S. Pat. No. 3,227,554 and the so-called DIR compounds described in U.S. Pat. No. 3,632,345.

The above mentioned DIR couplers and DIR compounds contain a thioether substituent in the coupling position, which substituent is split off as a diffusible mercapto compound in the colour coupling reaction. This mercapto compound has development inhibiting properties and is therefore capable of influencing the subsequent development of the silver halide. These DIR couplers are capable of improving the properties of photographic materials in several respects. They can be used to control the graininess, sharpness and gradation of the images and can bring about a substantial improvement in the colour reproduction as a whole.

Reference may be made in this connection to the article entitled "Development—Inhibitor—Releasing Couplers in Colour Photography" in "Photographic Science and Engineering" 13, 74 (1969).

The known DIR couplers inevitably give rise to a dye in addition to the released development inhibitor. The known DIR compounds, such as those described in the above mentioned U.S. Pat. No. 3,632,345 and German Offenlegungsschriften Nos. 2,359,295 and 2,405,442 do not, in any substantial extent, give rise to coloured compounds in their reaction with oxidized colour developers.

It has been found, however, that the known DIR compounds are frequently too unstable or in some cases, do not meet the requirement of giving rise only to colourless reaction products. In the first case, the development inhibitor is not released imagewise, and this is shown by a general loss in sensitivity. In the second case, unwanted side densities are built up.

There is also a shortage of DIR compounds of low reactivity which are particularly suitable for the following purposes by virtue of this property:

1. For use within a layer together with coloured couplers, masking couplers and white couplers;
2. for mixing with a more reactive DIR coupler in order to obtain a certain gradation curve or gradation;
3. for use in intermediate layers for the purpose of obtaining a high interimage effect (IIE) in the adjacent layers without at the same time causing a loss in sensitivity of the photographic material such as occurs when more highly reactive DIR compounds are used.

It is therefore an object of the present invention to provide new compounds which react with colour developer oxidation products to release development inhibiting substances. It is a particular object of this invention to find new DIR compounds of this kind which are particularly suitable for use in combination with more highly reactive DIR compounds for the purpose of producing a high edge effect and influencing the gradation curve and interimage effect, and which are particularly suitable for use in intermediate layers and give rise to colourless reaction products and are characterised by their high stability.

The problem outlined above is solved according to the invention by the preparation of new DIR compounds.

The invention relates to a photographic process in which an imagewise exposed colour photographic material comprising at least one light-sensitive silver halide emulsion layer is developed with a colour developer substance that contains a primary aromatic amino group and in which during said development step at least one thioether compound as defined hereinafter is present, which thioether compound is capable of releasing, on reaction with the colour developer oxidation products, a diffusible silver halide development inhibitor.

The invention further relates to a colour photographic material comprising at least one light sensitive silver halide emulsion layer and containing in said light sensitive layer or in a non-light sensitive binder associated thereto at least one non-diffusing thioether compound as defined hereinafter which thioether compound is capable of releasing on reaction with the colour developer oxidation products, a diffusible silver halide development inhibitor.

The thioether compound according to the present invention which may be contained in the developer solution or, what is more preferred, in non-diffusing form, in the photographic material may be represented by the following general formula I or its tautomeric form Ia:

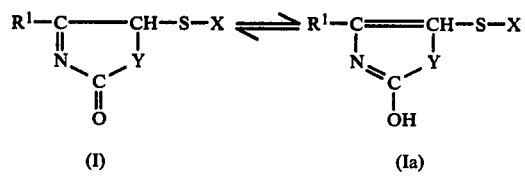

(I)    (Ia)

in which
R¹ represents a hydrocarbyl group
Y represents —S— or —NR², in which R² represents hydrogen, a hydrocarbyl group, a heterocyclic group attached through a ring carbon atom or, preferably an electron-attracting substituent such as —CN, alkoxycarbonyl, carbamoyl, sulphamoyl, alkyl sulphonyl, aryl sulphonyl, alkoyl or aroyl;
X represents an aliphatic group, an aromatic group or in particular a heterocyclic group which is split off with the sulphur atom or the thioether bridge to form a diffusible mercapto compound which inhibits the development of the silver halide.

By "hydrocarbyl group" is meant an aliphatic or aromatic hydrocarbon group, e.g. a substituted or unsubstituted alkyl or aryl group.

Examples of aliphatic hydrocarbon groups which R¹ and R² may represent include alkyl groups with from 1 to 18 carbon atoms which may be straight or branched chained or cyclic and may be substituted by alkoxy, aroxy, aryl, halogen, carboxyl or sulpho groups, such as methyl, isopropyl, tert.-butyl, dodecyl, heptadecyl, benzyl, phenylethyl, carboxy-tert.-butyl or methoxypropyl.

Examples of aromatic groups which R¹ and R² may represent include phenyl and naphthyl groups which may be substituted by one or more substituents, e.g. by alkyl, alkoxy, alkylamino, dialkylamino or alkylthio groups, in which the alkyl groups may contain from 1 to 20 carbon atoms; halogen such as chlorine or bromine; carboxyl, sulpho, nitro, cyano, acyl or acylamino, in which the acyl portion is derived from aliphatic or aromatic carboxylic or sulphonic acids, including substituted or unsubstituted carbamic acids and sulphamic acids.

The following are examples or substituted aromatic groups: Sulphohenyl, sulphonaphthyl, ω-sulphopropoxyphenyl; tetradecoxyphenyl; dodecylphenyl; t-butylphenyl; tetradecanoylaminophenyl; hexadecylthiophenyl; α-(2,4-di-t-pentylphenoxy)-butyramidophenyl; 2-tetradecyl-4-chloro-5-methylphenoxy-ethoxycarbonylaminophenyl; 2,4-di-t-pentylphenoxyacetylaminophenyl; α-sulphostearoylaminophenyl; 3-pentadecylphenoxy-ethoxycarbonyl-aminophenyl; 4-(1-octadecyl-5-sulphobenzimidazolyl-2-phenyl; 2-N-methyl-N-octadecylamino-5-sulphophenyl; N-phenyl-N-octadecylsulphamoylphenyl; tetradecylsulphonylphenyl; 2-tetradecocy-5-N-methylsulphonylphenyl; dimethylaminosulphonylphenyl; N-ethyl-N-octadecyl-carbamoylphenyl; N-phenylcarbamoylphenyl; 4-(α-Carboxymethyl)-phenyl; 4-(α-carboxy-methoxy)-phenyl; 3-(α-carbethoxy-methyl)-phenyl; 2-(α-tert.-butyloxycarbonylmethyl)-phenyl; 4-(α-carboxy-α-dodecylmethoxy)-phenyl; 4-(α-carboxy-α-octyl-methyl)-phenyl; 3-(α-dodecyloxycarbonyl-methoxy)-phenyl; 4-[(α-(o-tetradecyloxyphenyl-carbamoyl)-methyl]-phenyl; 4-(α-carboxy-N-methylamino)-phenyl and 3-(α-sulphomethyl)-phenyl).

The following are examples of heterocyclic groups which $R^1$ and $R^2$ may represent: 5- or 6-membered heterocyclic groups, preferably heteroaromatic groups, e.g. pyridyl, thienyl, thiazolyl, furanyl or indole groups.

The following are examples of aliphatic groups whic X may represent: Alkyl groups with 1 to 10 carbon atoms which may be unsubstituted or substituted by carboxyl and/or amino groups, such as

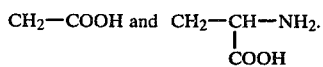

Examples of aromatic groups which X may represent include substituted or unsubstituted phenyl or naphthyl groups such as phenyl, carboxyphenyl and nitrophenyl.

The following are examples of heterocyclic groups which X may represent: 5- or 6-membered heteroaromatic groups having at least one nitrogen atom, e.g.
tetrazolyl, such as 1-phenyltetrazolyl, 1-nitrophenyltetrazolyl or 1-naphthyltetrazolyl;
triazolyl, such as 1-phenyl-1,2,4-triazolyl;
thiadiazolyl, such as 2-phenylamino-1,3,4-thiadiazolyl;
oxadiazolyl;
thiazolyl, includng benzothiazolyl and naphthothiazolyl;
oxazolyl, including benzoxazolyl and naphthoxazolyl, for example 7-sulphonaphtho-[2,3-d]-oxazolyl;
pyrimidyl, such as 4-methyl-6-aminopyrimidyl or 4-methyl-6-hydroxy-pyrimidyl; or
triazinyl, such as thiadiazolotriazinyl.

Compounds in which X represent a 1-phenyltetrazolyl group have been found to be particularly useful.

The DIR compounds according to the invention may be either soluble and diffusible or they may be incorporated in photographic materials in a diffusion resistant form. In the first of these cases, they preferably have at least one group which renders them soluble, e.g. at least one sulpho group, and are otherwise substantially free from groups which confer diffusion resistance. If they are required to be incorporated in the layers of the colour photographic material in a non-diffusible form the compounds according to the present invention contain at least one group which confers diffusion resistance.

By groups which confer diffusion resistance are meant groups which make it possible for the compounds according to the invention to be incorporated in diffusion-fast form in the hydrophilic colloids normally used in photographic materials. Particularly suitable groups for this purpose are organic groups generally containing straight or branched chain aliphatic groups, which may also contain isocyclic or heterocyclic aromatic groups. The aliphatic portion of these groups generally has form 8 to 20 carbon atoms. The groups are attached to the remainder of the molecule either directly or indirectly, e.g. through one of the following groups:

—CONH, —SO$_2$NH, —CO—, —SO$_2$—, —O—, —S— or —NR'—, wherein R' represents hydrogen or alkyl.

The group which confers diffusion resistance may in addition contain water-solubilizing groups, e.g. sulpho groups or carboxyl groups, and these may also be present in an anionic form. Since the diffusion property depends on the molecular size of the compound as a whole, it is in certain cases sufficient to use one or more shorter chain groups to confer diffusion resistance, such as t-butyl, cyclopentyl or isoamyl groups, for example if the molecule as a whole is large enough.

When thiazolinone compounds (Y=S) are to be incorporated in a diffusion-fast form, the group which confers diffusion resistance is situated on the substituent $R^1$. In the case of imidazolinone compounds (X=NR$^2$), there is the additional possibility of introducing the group which confers diffusion resistance into the substituent $R^2$.

Examples of particularly suitable DIR compounds based on thiazole are shown in Table 1 and examples of particularly suitable DIR compounds based on imidazole in Table 2.

Table 1

Thiazol-Type

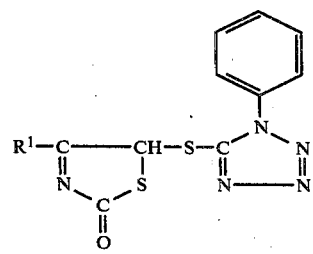

Table 1-continued
(8) 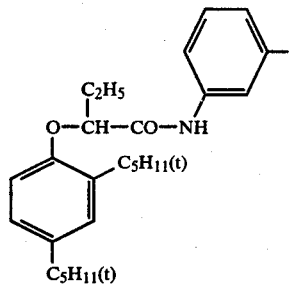
(9) 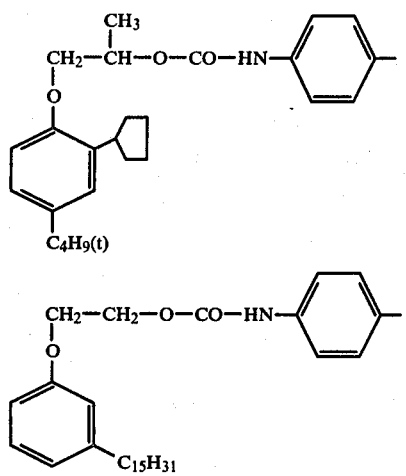
(10) 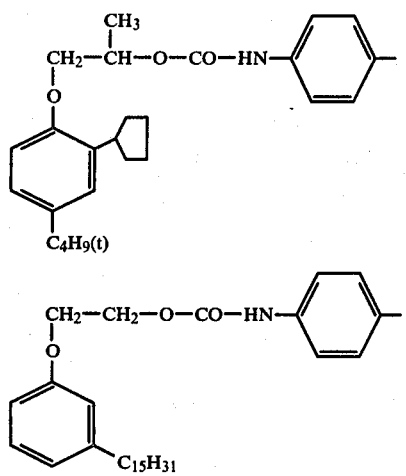
Table 2
Imidazol-Type
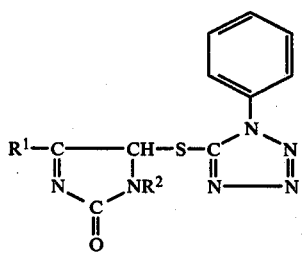
| Compound | R$^1$ | R$^2$ |
|---|---|---|
| 1 | 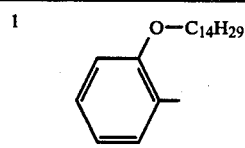 | |
| 2 | 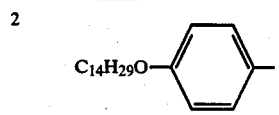 | |
| 3 | 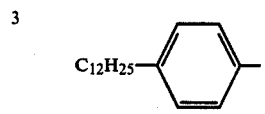 | |
| 4 | 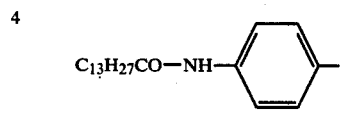 | |
| 5 | 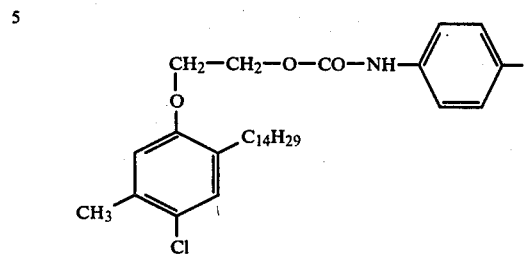 | |

Table 2-continued
Imidazol-Type
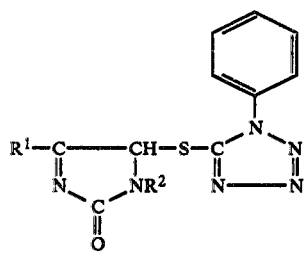
| Compound | R¹ | R² |
|---|---|---|
| (6) | 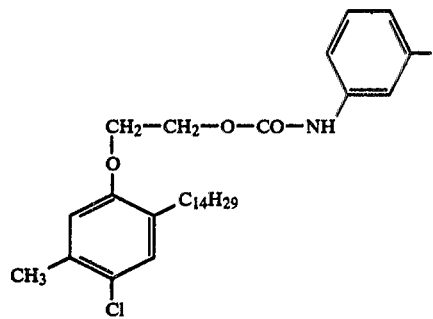 | |
| (7) | 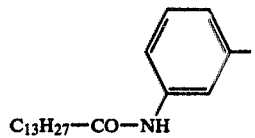 | |
| 11 |  | H |
| 12 |  | H |
| 13 | 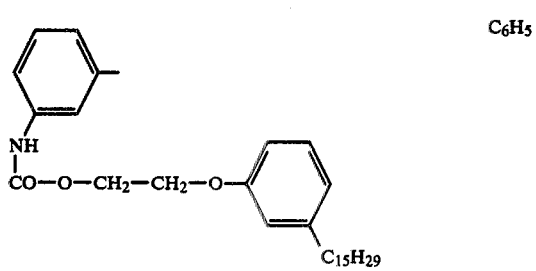 | $C_6H_5$ |
| 14 | 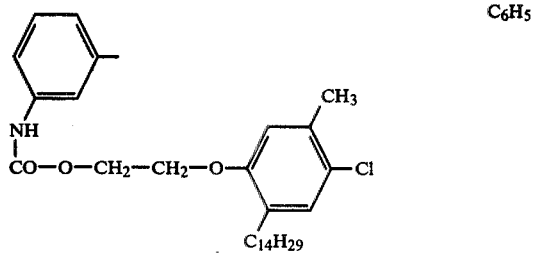 | $C_6H_5$ |

Table 2-continued
Imidazol-Type
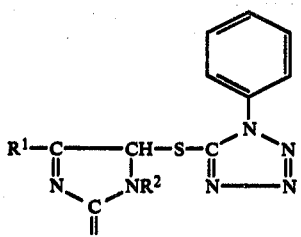
| Compound | R¹ | R² |
|---|---|---|
| 15 | 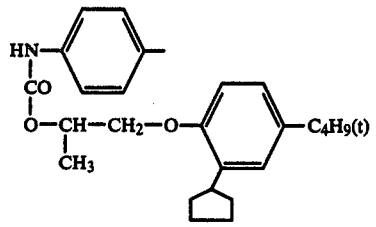 | H |
| 16 | 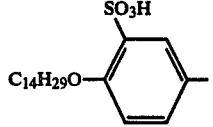 | H |
| 17 | 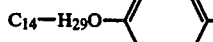 | 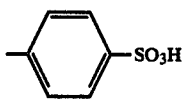 |
| 18 | 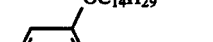 | $-COOC_2H_5$ |
| 19 | 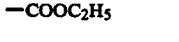 | $-COOC_{14}H_{29}$ |
| 20 |  | $-SO_2CH_3$ |
| 21 | $C_6H_5$ |  |
| 22 | $C_6H_5$ | 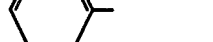 |
| 23 | $C_6H_5$ |  |
| 24 | $C_6H_5$ |  |

Table 2-continued
Imidazol-Type

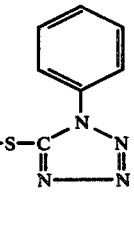

| Compound | R¹ | R² |
|---|---|---|
| 25 | $C_6H_5$ | 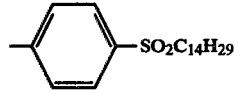 |
| 26 | $C_6H_5$ | 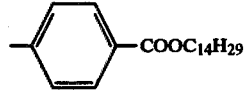 |
| 27 | 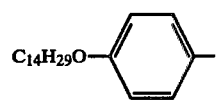 | 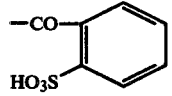 |
| 28 | 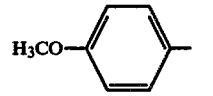 | 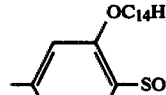 |
| 29 | $C_4H_9(t)$ | 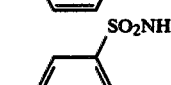 |
| 30 | 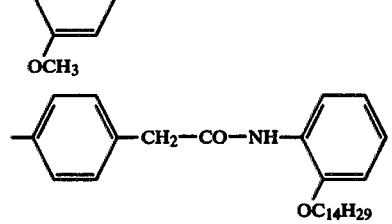 | 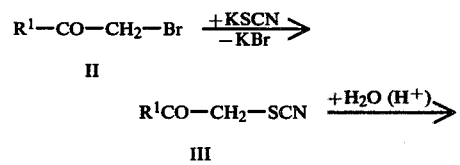 |

Preparation of the compounds according to the invention represented by the general formula I is carried out by reacting the appropriate thiazolinone or imidazolinone derivatives with 1-phenyl-5-mercaptotetrazole in glacial acetic acid as described in the following example.

Compounds according to the invention represented by the general formula I in which Y represents S are prepared from suitable halogenated ketones II by reacting with KSCN in alcoholic solution to convert them into the thiocyanate compounds III. The latter may then be cyclised to the 2-hydroxythiazole compound Ia by the catalytic action of H⁺ ions (sulphuric acid) in approximately 90% glacial acetic acid.

$$R^1\text{—CO—CH}_2\text{—Br} \xrightarrow[-KBr]{+KSCN}$$

II $$R^1\text{CO—CH}_2\text{—SCN} \xrightarrow{+H_2O\ (H^+)}$$

III

-continued

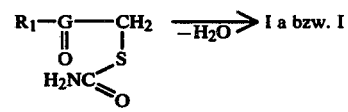 I a bzw. I

Compounds according to the invention represented by the general formula I in which Y represents NR² are generally also prepared from the corresponding ω-halogen ketones. One of the following three methods of synthesis (Z represents halogen) is recommended, depending on the nature of the substituent R²:

1. For R²=H, alkyl or aryl, the ω-halogen ketone is reacted with the corresponding amine H₂N—R² to form the ω-amino-ketone which is then cyclised to the imidazolinone by KOCN in accordance with the following reaction equation:

$$R^1\text{—CO—CH}_2Z + HNH\text{—}R^2 \longrightarrow$$

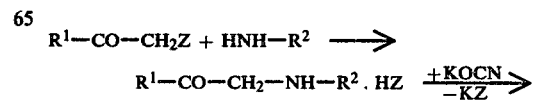

-continued

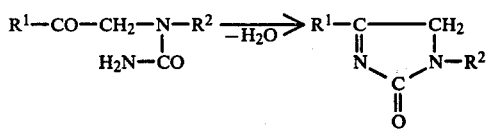

2. For compounds in which $R^2$ represents COOR, $-SO_2-R$ or $-CO-R$, the parent compound in which $R^2$ represents H is used as starting material. This is reacted with the appropriate acid chlorides in basic solvents as follows:

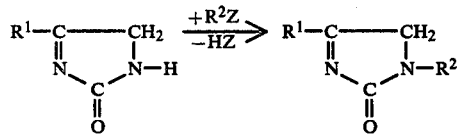

3. Compounds in which $R^2$ represent CN may be synthesised from the appropriately substituted urea in accordance with the followed reaction scheme

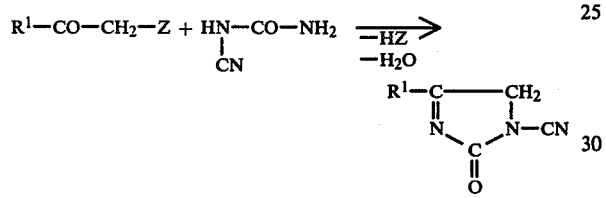

Methods described in the literature may also be used, for example those reported in Chem. Ber. 99, 2113 (1966) and in Chemistry Letters, pages 401–404 (1974), published by the Chemical Society of Japan. Preparation of compound 2

A solution of 14.85g(0.11 mol) of sulphuryl chloride in 20 ml of glacial acetic acid is added to 19.6 g (0.11 mol) of 1-phenyl-5-mercapto-tetrazole in 150 ml of glacial acetic acid with stirring. The mixture is first stirred at room temperature for 30 minutes and then at 40° C. for another 30 minutes.

The clear yellow solution thereby obtained is then added to a solution of 38.9 g (0.1 mol) of 4-(o-tetradecyloxy-phenyl)-2-hydroxythiazole in 1000 ml of glacial acetic acid at approximately 60° C. with stirring. 2000 ml of water are added to the reaction mixture after 2 hours, and the product which preciptates is taken up in ethyl acetate. The solution in ethyl acetate is separated off, washed several times with water and evaporated to dryness. The residue is recrystallised from propanol. 37.5g of compound 2 are obtained. Mp.: 97° C.

The other thiazole compounds are converted into the corresponding DIR compounds according to the invention in similar manner. Preparation of compound 12

Stage 1

88 g of p-tetradecyloxy-ω-bromoacetophenone are dissolved in 320 ml of anhydrous chloroform. 30.4 g of urotropine are added at room temperature. The solution heats up spontaneously. It is then stirred for 2 hours at room temperature. The chloroform is evaporated off and the solid residue is triturated with acetone. The crystalline precipitate is suction filtered and washed several times with acetone. The crude product is then introduced into a solution of 140 ml of concentrated hydrochloric acid in 1000 ml of ethanol and stirred for 24 hours at room temperature. The product is suction filtered and washed with a mixture of ethanol and concentrated hydrochloric acid (7:1). 80 g =95% of p-tetradecyloxy-ω-aminoacetophenone-hydrochloride melting at 190° to 195° C. are obtained.

Stage 2

80 g of the compound obtained as described above are dissolved hot in a mixture of 920 ml of ethanol and 380 ml of water. A solution of 80 g of KOCN in 300 ml of water are added and the mixture is boiled under reflux for 2 hours. The precipitated product is suction filtered after cooling. 75 g, corresponding to 95%, of 4-(p-tetradecyloxyphenyl)-imidazolinone, m.p. 129° to 135° C., are obtained.

Stage 3

A solution 14.85 g (0.11 mol) of sulphuryl chloride in 20 ml of glacial acetic acid is added to 19.6 g (0.11 mol) of 1-phenyl-5-mercapto-tetrazole in 150 ml of glacial acetic acid with stirring. The mixture is first stirred at room temperature for 30 minutes and then at 40° C. for a further 30 minutes. The sulphenyl chloride thus obtained is introduced into a preheated suspension of 37.3 g of 4-p-tetradecyloxyphenylimidazoline (stage 2 above) in 450 ml of glacial acetic acid. The mixture is left to react for 4 hours at 40° C. and then for 60 hours at room temperature. Undissolved constituents are removed by filteration and the filtrate is poured on 3 liters of ice water. The precipitate thereby formed is suction filtered, washed with water until neutral, again suspended in 300 ml of methanol to remove unreacted 1-phenyl-5-mercaptotetrazole, and suction filtered.

46 g (86% of the theory) of compound 12, m.p. 121° to 127° C., are obtained.

Preparation of compound 18

Stage 1

41 g of 2-tetradecyloxy-ω-bromoacetophenone are dissolved in 250 ml of anhydrous acetonitrile at 70° C. with stirring. 15 g of cyanimidocarboxylic acid ethyl ester in 25 ml of acetonitrile are added and the mixture is heated to boiling for 4.5 hours. After it has been left to stand for 48 hours, the precipitate is suction filtered and washed with a mixture of petroleum hydrocarbons which has been heated to 50° C. The filtrates are collected and evaporated, and the oil which remains behind is taken up in 150 ml of saturated methanolic hydrochloric acid. The precipitate which forms is suction filtered, washed with methanol and recrystallised from 350 ml of methanol.

Yield: 13 g (31%), m.p. 112° to 115° C.

Stage 2

The solution of 0.11 mol of sulphenyl chloride of the 1-phenyl-5-mercaptotetrazole prepared as described for compound 2 is added dropwise to 44 g of the compound described above in 1000 ml of glacial acetic acid. An exothermic reaction starts, which is accompanied by the formation of a green colour. The mixture is stirred at 40° C. for 8 hours and then left to stand overnight. It is then poured on 3 liters of water and the oily product thereby precipitated is taken up in ethyl acetate and washed several times with water and finally with dilute hydrochloric acid. Removal of the ethyl acetate by evaporation leaves a yellow oil which becomes solid when triturated with 100 ml of petroleum hydrocarbons boiling at 50° C. When the residue is suction filtered and washed with petroleum hydrocarbons, 36 g (59% of the theory) of compound 18 melting at 73 to 78° C. are obtained.

Preparation of compound 19

Stage 1

16 g (0.1 mol) of 2-hydroxy-4-phenylimidazole are suspended in a mixture of 150 ml of dimethylacetamide and 16 ml of pyridine at room temperature with stirring.

55 g (0.2 mol) of tetradecyl chloroformate are added dropwise with stirring. A pale red colour develops with evolution of heat and all of the components go into solution. When the solution is subsequently heated to 60° C., a thick crystalline paste of compound 43 slowly precipitates. The product is suction filtered, washed with methanol and with a mixture of 90 ml of methanol and 30 ml of 10% hydrochloric acid, and then recrystallised from ethyl acetate.

19 g (47% of the theory) of 2-hydroxy-4-phenyl-1-tetradecyloxycarbonylimidazole, m.p. 166° to 171° C., are obtained.

Stage 2

The solution of 0.11 mol of sulphenyl chloride of 1-phenyl-5-mercaptotetrazole prepared as described for compound 2 is added dropwise to a suspension of 40 g (0.1 mol) of 2-hydroxy-4-phenyl-1-tetradecyloxycarbonyl imidazole (stage 1 described above) in 450 ml of glacial acetic acid. The mixture is stirred at 40° C. for 4 hours and then left to stand overnight and processed in the same way as compound 12. After recrystallisation from methanol, 37.2 g (67% of the theory) of compound 19, m.p. 110° to 115° C., are obtained.

The other imidazole DIR compounds according to the invention may be prepared in similar manner. The compounds according to the invention are comparable to the known DIR couplers and DIR compounds in that, like them, they are thioether compounds which react with colour developer oxidation products to release a diffusible mercaptan which inhibits the development of silver halide. According to U.S. Pat. No. 3,148,062, DIR couplers are subdivided into those in which the group which can be released already has an inhibitory action before the coupling reaction and those in which the inhibitory action comes into being only when a molecular group is released from the coupling solution. In the latter case, the inhibitor is said to be non-preformed. In keeping with this terminology, the compounds according to the invention should also be described as thioether compounds with react with colour developer oxidation products to releasea diffusible non-preformed development inhibitor.

Compound with known DIR compounds, the compounds according to the invention are distinguished by their high stability, colourless reaction products and their special suitability for use as mixtures with more highly reactive DIR compounds for the purpose of controlling the gradation, graininess and sharpness and for producing an edge effect and interimage effect.

Among the thioether compounds of the present invention some are found which have a desired low reactivity. Although generally DIR compounds are used having as high a reactivity as possible, it is desirable also to have at hand for some special purposes DIR compounds of a low reactivity. As to this we refer to our copending German Pat. application P 27 04 797.8 and to the corresponding U.K. and U.S. patent applications.

The DIR compounds according to the invention are particularly suitable for use in those colour photographic multilayer materials in which the silver halide, after it has been exposed imagewise, is developed by the usual colour developers, e.g. by the usual aromatic compounds based on p-phenylene diamine and containing at least one primary amino group.

The following are examples of suitable colour developers:

N,N-dimethyl-p-phenylenediamine,
N,N-diethyl-p-phenylenediamine,
Monomethyl-p-phenylenediamine,
2-amino-5-diethylaminotoluene,
N-butyl-N-ω-sulphobutyl-p-phenylenediamine,
2-amino-5-(N-ethyl-N-β-methanesulphonamidoethyl-amino)toluene,
N-ethyl-N-β-hydroxyethyl-p-phenylenediamine,
N,N-bis-(β-hydroxyethyl)-p-phenylenediamine and
2-amino-5-(N-ethyl-N-β-hydroxyethylamino)-toluene.

Other suitable colour developers have been described, for example, in J. Amer. Chem. Soc. 73, 3100 (1951).

The developer compounds are usually introduced into an alkaline development bath which is used for treating the colour photographic material after it has been exposed imagewise, but they may also be incorporated in one or more layers of the photographic material. In the latter case, the developer compounds may contain groups which render them diffusion resistant and they may be situated in a layer which also contains a diffusion resistant colour coupler or a diffusion resistant colour providing compound, for example as described in U.S. Pat. No. 3,705,035.

In tht case, development merely requires the use of an alkaline activator solution containing an auxiliary developer such as phenidone. The oxidation product of the colour developer produced on development reacts with the non-diffusible colour coupler to form a non-diffusible image dye. At the same time, the oxidation product of the colour developer reacts with the non-diffusible DIR compounds according to the invention which are present at the same time, to release diffusible inhibitor substances.

The colour photographic multilayered material according to the invention contains a compound of the formula I in at least one of its layers. This DIR compound may be incorporated in a light-sensitive silver halide emulsion layer or it may be situated in a hydrophilic layer of binder which is associated with such a light-sensitive silver halide emulsion layer but need not itself be light-sensitive. The term "associated" is applied in this context to a layer which is in such spatial relationship to the light-sensitive silver halide emulsion layer that significant quantities of colour developer oxidation products may occur in it due to diffusion from the light-sensitive silver halide emulsion layer when development takes place in this silver halide emulsion layer.

The concentration of DIR compound according to the invention in a layer may vary within wide limits, e.g. from $1 \times 10^{-3}$ to $300 \times 10^{-3}$ mol per kg of silver halide emulsion or from $0.05 \times 10^{-3}$ to $1 \times 10^{-3}$ mol per gram of binder in an associated layer of binder. The quantity depends on the particular purpose for which the DIR compound is used, on the particular type of silver halide emulsion, and on whether the DIR compound is contained in a silver halide emulsion layer or in a light insensitive layer of binder. It is advantageous that the upper limit can be kept lower than the concentrations at which the colour couplers are used in the photographic layers, since the compounds according to the invention produce excellent effects even at low concentrations.

The concentration at which the DIR compound according to the invention should be used in processing solutions such as developers depends on the desired effect and on the photographic materials used and on the emulsions obtained in them, and it can easily be determined with the aid of a few laboratory tests.

The compounds according to the invention may be used in the yellow, magenta or cyan layer of a multilayered colour photographic material as well as in a light-insensitive layer adjacent to such layers since, in modern photographic recording materials, high interimage effects, improvements in the graininess and increase in the sharpness by improvement of the edge effect are desirable in all light-sensitive colour forming layers.

The inhibitory action of the compounds used according to the invention may occur both in the layer which contains the compounds according to the invention, provided this layer contains developable silver halide, and in adjacent silver halide emulsion layers into which the released inhibitor is capable of diffusing. In this way, the compounds according to the invention can be used to control the development process in all of the individual light-sensitive silver halide emulsion layers in various ways, and it is even possible to influence the development of one silver halide emulsion layer by the result of imagewise development in another layer by virtue of the vicinal effects which can be achieved with the compounds according to the invention, so that an overall improvement in graininess, sharpness and colour reproduction can be achieved. It is also of interest to use the DIR compounds according to the invention in so-called double layers of a multilayered material. These double layers together form a partial colour unit which, for the purpose of obtaining greater sensitivity and a finer grain, are arranged in two superimposed layers in a multilayered combination, for example as described in German Offenlegungsschrift No. 2,439,424. A double layer combination forming a partial colour unit generally comprises a coarse-grained, high sensitivity layer containing a comparatively small quantity of colour coupler arranged above a less sensitive layer containing an excess of colour coupler.

In order to achieve the desired effects, such as improvement in the graininess or sharpness and to obtain an interimage effect, the DIR compounds according to the invention may be added to either one of both of the two layers. They are preferably added to the lower, fine grained layer of a double layer combination.

The light-sensitive silver halide emulsion layers of the photographic material according to the invention have differing spectral sensitivities and each of them has associated with it at least one non-diffusible compound for producing an image dye of a colour which is generally complementary to that of the spectral sensitivity. These compounds may be conventional colour couplers, which are generally incorporated in the silver halide layers. Thus the red sensitive layer, for example, contains a non-diffusible colour coupler for producing the cyan partial colour image, generally a coupler based on phenol or α-naphthol; the green sensitive layer contains at least one non-diffusible colour coupler for producing the magenta partial colour image, usually colour couplers based on 5-pyrazolone or indazolone; lastly, the blue sensitive layer unit contains at least one non-diffusible colour coupler for producing the yellow partial colour image, generally a colour coupler having an open chain ketomethylene group. Large numbers of colour couplers of these kinds are known and have been described in numerous patent specifications as well as in other publications, for example in "Farbkuppler" by W. Pelz in "Mitteilungen aus den Forschungs-laboratorien der Agfa, Leverkusen/Munchen", Volume III (1961) and by K. Venkataraman in "The Chemistry of Synthetic Dyes", Vol. 4, 341–387 Academic Press 1971.

The non-diffusible colour couplers may contain a releasable substituent in the coupling position so that, in contrast to the usual 4-equivalent couplers, they require only two equivalent of silver halide to produce the colour. The colour couplers themselves are usually colourless. If, however, the releasable substituent contains a chromophoric group, as in the known masking couplers, then the colour couplers generally have a colour which is suitable for masking unwanted side densities of the image dye in accordance with conventional masking techniques. The image dyes produced from colour couplers are generally resistant to diffusion.

The image dyes may, however, initially be produced in a diffusible form in the process of development and fixed only subsequently, after they have been transferred to an image receiving layer, as in the case with various dye diffusion transfer processes, e.g. those described in U.S. Pat. Nos. 3,227,550 and 3,628,952 and in German Patent No. 1,772,929. In these cases, colourless or coloured, non-diffusible, colour providing compounds which release diffusible dyes in imagewise distribution when development takes place are associated with the light-sensitive silver halide emulsions. These colour providing compounds are incorporated either in the silver halide emulsion layer or in an associated hydrophilic binder layer which may, for example, contain development nuclei and may also contain silver halide which is developable without exposure.

When conventional silver halide emulsions are used in combination with non-diffusible colour couplers or with non-diffusible colour providing compounds, negative colour images are normally obtained. However, the DIR compounds according to the invention as well as the DIR couplers may also advantageously be used in reversal processes for producing positive images. The process employed may be conventional reversal process in which the photographic material is first subjected to black-and-white development after imagewise exposure and is then colour developed after a diffuse second exposure, or it may be a special reversal process in which the imagewise information in the photographic material is reversed due to the pesence of the DIR compounds according to the invention. Such reversal can be obtained if a silver halide emulsion layer which can develop spontaneously, i.e. without exposure to light, and which contains a colour providing compound is arranged, for example, adjacent to a conventional silver halide emulsion layer containing a DIR compound. It will be obvious that DIR couplers or DIR compounds used for such a procedure must be capable of releasing the inhibitor very rapidly so that it will inhibit development imagewise in the spontaneously developable layer.

The non-diffusible colour couplers and colour providing compounds as well as the non-diffusible development inhibitor releasing compounds used according to the invention are added to the light-sensitive silver halide emulsions or to other casting solutions by the usual, known methods. If they are water-soluble or alkali soluble compounds, they may be added to the emulsions in the form of aqueous solutions, to which water-miscible organic solvents such as ethanol, acetone or dimethyl formamide may be added. If the non-diffusible colour couplers, colour producing compounds or development inhibitor releasing compounds used are insoluble in water or alkalies, they may be emulsified in known manner, for example by adding a solution of the compound in a low boiling organic solvent directly to the silver halide emulsion or first to an aqueous gelatine emulsion and then removing the organic solvent in the usual manner. The resulting emulsion of the given compound in gelatine is then mixed with the silver halide emulsion. If desired, so-called coupler solvents or oil formers may also be added to assist emulsification of such hydrophobic compounds. These coupler solvents or oil formers are generally higher boiling organic compounds which form oily droplets in which the non-diffusible colour couplers and development inhibitor releasing compounds which are required to be emulsified in the silver halide emulsions become enclosed. Information on this may be found, for example, in U.S. Pat. Nos. 2,322,027; 2,533,514; 3,689,271; 3,764,336 and 3,765,897. If the compounds according to the invention are emulsified in the layers with the aid of such oil formers, the diffusion resistance conferring groups used in the compounds according to the invention need not be so powerful as is otherwise necessary; in this case, shorter alkyl groups such as t-butyl or isoamyl groups are sufficient to prevent diffusion of the compounds according to the invention in the layers of the photographic material.

The usual silver halide emulsions are suitable for the present invention. The silver halide contained in them may be silver chloride, silver bromide or mixtures thereof, which may have a small silver iodide content of up to 20 mol %. The emulsions may be ordinary negative emulsions or they may be direct positive emulsions, i.e. those which have a high sensitivity in the interior of the silver halide grains, for example, the emulsions described in U.S. Pat. No. 2,592,250.

The binder used for the photographic layers is preferably gelatine but this may be partly or completely replaced by other natural or synthetic binders. Suitable natural binders include e.g. alginic acid and its derivatives such as its salts, esters or amides, cellulose derivatives such as carboxymethylcellulose, alkylcelluloses such as hydroxyethylcellulose, starch or its derivatives such as its ethers or esters, or carrageenates. Suitable synthetic binders include polyvinyl alcohol, partially saponified polyvinyl acetate and polyvinyl pyrrolidone.

The emulsions may also be chemically sensitized, e.g. by adding sulphur compounds such as allylisothiocyanate, allylthiourea or sodium thiosulphate at the chemical ripening stage. Reducing agents may also be used as chemical sensitizers, e.g. the tin compounds described in Belgian Pat. Specifications No. 493,464 and 568,687 or polyamines such as diethylene triamine or aminomethane sulphinic acid derivatives, e.g. according to Belgian Pat. Specification No. 547,323.

Noble metals such as gold, platinum, palladium, iridium, ruthenium or rhodium and compounds of these metals are also suitable chemical sensitizers. This method of chemical sensitization has been described in the article by R. Koslowsky in Z. Wiss. Phot. 46, 65 to 72 (1951).

The emulsions may also be sensitized with polyalkylene oxide derivatives, e.g. with a polyethylene oxide having a molecular weight of between 1000 and 20,000 or with condensation products of alkylene oxides and aliphatic alcohols, glycols or cyclic dehydration products or hexitols, with alkyl substituted phenols, aliphatic carboxylic acids, aliphatic amines, aliphatic diamines and amides. The condensation products have a molecular weight of at least 700, preferably more than 1000. These sensitizers may, of course, also be used in combination in order to obtain special effects, as described in Belgian Pat. Specification No. 537,278 and British Pat. Specification No. 727,982.

The emulsions may also be spectrally sensitized, e.g. with the usual monomethine or polymethine dyes such as acid or basic cyanines, hemicyanines, streptocyanines, merocyanines, oxonoles, hemioxonoles, styryl dyes or others, including trinuclear or higher nuclear methine dyes, for example, rhodacyanines or neocyanines. Sensitizers of this kind have been described, for example, in the work by F. M. Hamer "The Cyanine Dyes and Related compounds" (1964), Interscience Publishers John Wiley and Sons.

The emulsions may contain the usual stabilizers, e.g. homopolar compounds or salts of mercury which have aromatic or heterocyclic rings, such as mercaptotriazoles, simple mercury salts, sulphonium mercury double salts and other mercury compounds. Azaindenes are also suitable stabilizers, particularly tetra- and penta-azaindenes and especially those which are substituted with hydroxyl or amino groups. Compounds of this kind have been described in the article by Birr in Z. Wiss. Phot. 47, 2 to 27 (1952). Suitable stabilizers also include the heterocyclic mercapto compounds, e.g. phenylmercaptotetrazole, quaternary benzothiazole derivatives and benzotriazole.

The emulsions may be hardened in the usual manner, for example with formaldehyde or halogenated aldehydes containing a carboxyl group, such as mucobromic acid, diketones, methane sulphonic acid esters and dialdehydes.

The photographic layers may also be hardened with epoxy hardeners, heterocyclic ethyleneimine hardeners or acryloyl hardeners. Examples of such hardeners have been described, for example, in German Offenlengunsschrift No. 2,263,602 and British. Patent Specification No. 1,266,655. The layers may also be hardened by the process according to German Offenlegungsschrift No. 2,218,009 in order to obtain colour photographic materials which are suitable for high temperature processing.

The photographic layers or colour photographic multilayered materials may also be hardened with diazine, triazine or 1,2-dihydroquinoline hardeners as described in British Pat. Nos. 1,193,290; 1,251,091;

1,306,544 and 1,266,655, French Pat. No. 7,102,716 or British Pat. No. 1,452,669.

Examples of such hardeners include diazine derivatives having alkyl or aryl sulphonyl groups, derivatives of hydrogenated diazines or triazines such 1,3,5-hexahydrotriazine, fluorosubstituted diazine derivatives, e.g. fluoropyrimidines and esters of 2-substituted 1,2-dihydroquinoline-or 1,2-dihydroisoquinoline-N-carboxylic acids. Vinylsulphonic acid hardeners and carbodiimide or carbamoyl hardeners are also useful, e.g. those described in German Offenlegungsschriften Nos. 2,263,602; 2,225,230 and 1,808,685; French Pat. No. 1,491,807; German Patent No. 872,153 and DDR Pat. Specification No. 7,218. Other suitable harderners have been described, for example, in British Pat. Specification No. 1,268,500.

The materials according to the invention may be, for example, positive, negative or reversal materials having the usual layer substrates used in known manner for the preparation of photographic materials. Suitable substrates include, for example, foils of cellulose nitrate; cellulose acetates such as cellulose triacetate; polystyrene; polyesters such as polyethylene terephthalate, polyolefines such as polyethylene or polypropylene, baryta paper or paper laminated with polyolefine, e.g. polyethylene laminated paper substrates and glass.

EXAMPLES

The DIR compounds are preferably used in multilayered arrangements such as those conventionally used, for example, for the preparation of light-sensitive negative or positive colour photographic materials.

The effect of the DIR compounds according to the invention is illustrated with the aid of the example of an arrangement of layers or partial layers typically used for colour negative materials.

Light-sensitive photographic material:

Arrangement of layers: Substrate: substrated cellulose triacetate support.
(a) Intermediate layer of gelatine (1μ)
(b) Cyan layer consisting of a silver halide emulsion (mixture of 70% of a high sensitivity emulsion and 30% of a relatively low sensitivity emulsion) which is sensitized to the red spectral region, and a colour coupler for cyan (silver application: 4 g Ag/m²);
(c) Intermediate layer of gelatine (1μ)
(d) Magenta layer consisting of a silver halide emulsion (mixture of 70% of a high sensitivity emulsion and 30% of a relatively low sensitivity emulsion) sensitized to the green spectral region, and a colour coupler for magenta (silver application: 3.5 g Ag/m²);
(e) Intermediate layer of gelatine (1μ);
(f) yellow filter layer (2μ);
(g) Yellow layer consisting of a silver halide emulsion (mixture of 50% of a high sensitivity emulsion, 25% of a medium sensitivity emulsion and 25% of a low sensitivity emulsion) which is sensitive to the blue spectral region, and a colour coupler for yellow (silver application 1.5 g Ag/m²);
(h) Protective layer of gelatine (1μ).

The material is hardened in the usual manner, e.g. with a carbodiimide hardener. The individual partial layers which are sensitive to red (b), green (d) and blue (g) are prepared by casting the following solutions:
(b) 1 kg of a red sensitized silver halide emulsion (100 g of Ag/kg of emulsion) in which the silver halide consists of 95 mol % of silver bromide and 5 mol % of silver iodide, 50 ml of a 1% solution of 1,3,3a,7-tetraza-4-hydroxy-6-methyl indene in methanol, 360 g of a coupler dispersion of a solution of 15 g of the cyan coupler represented by the following formula:

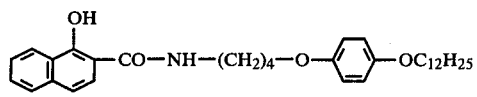

in 7.5 g of dibutylphthalate and
30 g of diethylcarbonate,
100 ml of a 4% aqueous gelatine solution,
0.8 g of Mersolat ® (wetting agents, sulphonated paraffin hydrocarbons),
10 ml of a 10% aqueous saponin solution
1000 ml of water.
(d) The composition of the casting solution for the green sensitive layer is similar to that used for the red-sensitive layer (b) but the emulsion is sensitized to the green region of the spectrum and, instead of cyan coupler dispersion, it contains 192 g of a dispersion of a magenta coupler represented by the following formula

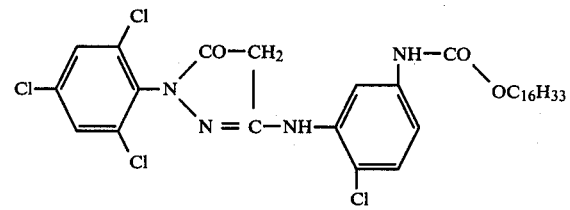

similar in composition to that of the cyan coupler dispersion of layer b).
(g) The composition of the casting solution for the blue-sensitive layer is similar to that used for the red-sensitive layer (b) but the emulsion is sensitive only to the blue region of the spectrum and, instead of cyan coupler dispersion, it contains 175 g of a 5% solution of yellow coupler represented by the following formula

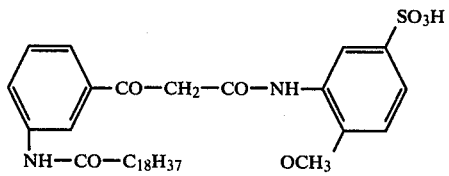

in an aqueous 8% gelatine solution.

Gelatine layers (a), (c), (e) and (h) are prepared by casting the following solution:
125 ml of a 10% gelatine solution,
500 ml of water
5 ml of a 10% aqueous solution of saponin.

The casting solution for the yellow filter layer is the same as the casting solution for gelatine layers (a), (c), (e) and (h) except for the addition of 1.4 g of finely dispersed metallic silver of the kind commonly used as barrier filter for the blue spectral portion of light.

Processing

The material is exposed in a conventional sensitometer behind a grey tep wedge and behind the colour separation filters blue, green and red, respectively, and is then developed in a colour developer having the following composition:

2 g of the sodium salt of isopropanoldiaminotetracetic acid,
30g of potash,
4g of potassium sulphite,
1.5 g of potassium bromide,
2 g of hydroxylamine and
5 g of colour developer represented by the following formula

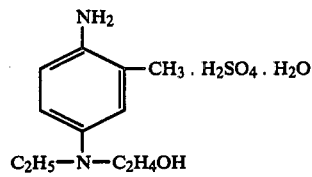

made up to 1 liter. pH adjusted to 10.2 Development: 3¼ minutes at 38° C.

The subsequent processing steps indicated below are each carried out for 3¼ minutes. The bath temperature is again 38° C. in each case.
Short stop bath:
  30 ml of acetic acid (concentrated)
  20 g of sodium acetate,
  water up to 1 liter
Washing
Bleach bath:
  100 g of potassium ferricyanide,
  15 g of potassium bromide,
  water up to 1 liter
Washing
Fixing bath:
  20% aqueous solution of sodium thiosulphate
Final washing.

Assessment of the exposed and developed samples:

Since the materials used in the experiments are not masked, the side densities of the dyes produced interfere with the determination of the true IIE. To eliminate the interference caused by the side densities, gradation curves are drawn up from the analytical densities obtained by converting the measured integral densities. The $\gamma$-values on which the IIE measurement is based are read off these analytical colour density curves. The IIE is defined as follows:

$$IIE = \frac{\gamma_s - \gamma_w}{0.6} \cdot 100\%$$

s: selective exposure
w: white exposure.

The graininess is given in $\rho_D$-values (rms-values obtained with a shutter diameter of 29$\mu$) obtained by the method described by H. T. Buschmann in "Bestimmung der Körnigkeit photographischer Schichten mit Hilfe digitaler Technik" in Optik 38, 1973, pages 169–219.

Dispersion of the DIR compounds is carried out as follows:

A solution of 10 g of DIR compound in 10 g of dibutyl phthalate, 30 ml of ethyl acetate and 5 g of dimethylformamide is emulsified in a solution of 100 ml of a 5% aqueous gelatine solution and 0.8 g of Mersolat (wetting agent: sulphonated paraffin hydrocarbons) with the aid of intensive mixing in a mixing siren.

EXAMPLE 1

Incorporation of the DIR compounds in red-sensitive layer (b):

Arrangement of layers: consisting of layers (a), (b) and (c).

Sample 1: No DIR compound in layer (b)
Sample 2: The emulsified DIR compound 12 is added to the casting solution for layer (b) in an amount of 62.6 g per kg of emulsion.
Sample 3: DIR compound 2 is added to the casting solution for layer (b) in an amount of 65.6 g per kg of emulsion.

The samples are exposed to red light behind a step wedge and developed as indicated above. The DIR compounds flatten the gradation by their inhibitory action.

Table 3

|  | $\gamma$ | Graininess $\sigma D \cdot 10^{-2}$ at density $D = 1$ and $\gamma = 0.80$ |
| --- | --- | --- |
| Sample 1 | 1.41 | 2.5 |
| Sample 2 | 0.80 | 1.7 |
| Sample 3 | 0.95 | 1.9 |

If, when casting the layers, the thicknesses of the layers are modified so that all three samples have a gradation of 0.80, the samples which contain the DIR compounds have a substantially lower graininess than sample 1 (Table 3) at virtually the same sensitivity.

EXAMPLE 2

Incorporation of the DIR compound in the filter yellow layer of total layer arrangements (layers (a) to (h)):

To the filter yellow layer containing colloidal silver for producing a yellow density of 0.8 density units the quantity of emulsified DIR compound 18 required to provide 0.15 g of the DIR compound per m² was added. When the magenta gradations obtained on green exposure were compared with those obtained on white exposure, the filter yellow layer which contained the DIR compound showed an increase in the magenta IIE.

Table 4

| | | | Exposure | |
| --- | --- | --- | --- | --- |
| Sample | DIR compound in filter yellow layer | IIE % magenta | green magenta $\gamma_s$ | white magenta $\gamma_s$ |
| 1 | DIR compound 18 | 30 | 1.28 | 1.10 |
| 2 | — | 15 | 1.25 | 1.16 |

EXAMPLE 3

Incorporation of DIR compound 17 in cyan layer b and of DIR compound 12 in magenta layer (d):

DIR compound 17 is dissolved in water adjusted to pH 10 by the addition of 0.1N sodium hydroxide solution, and the pH is then reduced to 6.5 with 0.01 N sulphuric acid solution. DIR compound 17 is added to the casting solution for layer (b) in an amount of 8 g per kg of emulsion.

The emulsified DIR compound 12 is added to the casting solution for layer (d) in an amount of 65 g to 1 kg of emulsion. Another sample containing no DIR compound in layer (b) is prepared for comparison.

The samples are exposed to green and white light behind a step wedge and developed as described above. The effect of the DIR compound in the cyan layer on the magenta IIE is investigated.

Table 5

| | | | Exposure | |
|---|---|---|---|---|
| Sample | DIR compound | IIE % magenta | green magenta $\gamma_s$ | white magenta $\gamma_w$ |
| 1 | 17 in (b) 12 in (d) | 35 | 0.85 | 0.64 |
| 2 | No DIR compound in (b) Compound 12 in (d) | 17 | 0.83 | 0.73 |

EXAMPLE 4

Incorporation of DIR compound 3 in the intermediate gelatine layer (c):

A complete arrangement of layers (layers (a) to (h)) is prepared (as in Example 3, sample 1) with DIR compound in the intermediate layer (c), i.e. between the red-sensitive and the green-sensitive layer.

The casting solution for the modified gelatine layer (c) has the following composition:
100 ml of a 10% gelatine solution
18.5 g of emulsified DIR compound 3
170 ml of water
5 ml of a 10% aqueous solution of saponin.

The layer is applied in a thickness of 1.0µ. DIR compound 3 is graded as a coupler having a relatively low reactivity.

Another complete arrangement of layers but without DIR compound in the usual intermediate layer (c) is prepared for comparison (sample 2).

The samples are exposed to red, green and white light behind a step wedge and processed as described above.

It is found that on exposure to red light, i.e. when developing the cyan layer b), partial development of the magenta layer (d) such as occurs to a certain extent in sample 2 is completely prevented by the presence of the DIR compound in layer (c). In the same way, the presence of the DIR compound in intermediate layer (c) also completely prevents partial development of the cyan layer (b) on exposure to green light, i.e. during development of the magenta layer (d). The DIR compound acts as a white coupler or oxform interceptor by intercepting the diffusible oxidation product.

Coupling of the DIR compound with the diffusible oxidation product releases inhibitor which diffuses into the adjacent red-sensitive or green-sensitive layers where it inhibits development. The IIE is thereby increased both in the cyan layer and in the magenta layer, as shown in the following Table.

Table 6

| | IIE% | | | White exposure | |
|---|---|---|---|---|---|
| Sample | Cyan/ magenta | Red exposure Cyan $\gamma_s$ | Green exposure magenta $\gamma_s$ | cyan $\gamma_w$ | magenta $\gamma_w$ |
| 1 | 53  45 | 0.91 | 0.81 | 0.59 | 0.54 |
| 2 | 35  30 | 0.99 | 0.86 | 0.78 | 0.68 |

The sensitivity can be measured in terms of the inertia speed, that is to say the relative log I.t. value obtained as point of intersection of the extrapolated straight line part of the characteristic curve with the fog density. If this criterion of sensitivity is used, one loses at the most 0.1 log I.t. units of magenta and cyan sensitivity if a relatively slowly coupling DIR compound such as DIR compound 3 is used in intermediate layer c). If instead of the relatively slowly coupling DIR compound 3 a relatively fast coupling compound, e.g. a DIR coupler of the following formula

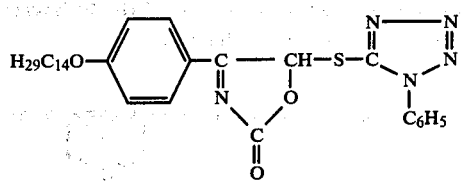

is used in a quantity resulting in much the same magenta and cyan gradations, substantially higher sensitivity losses, up to 0.3 log I.t. units, are recorded in magenta and cyan.

We claim:

1. A process of development in which an imagewise exposed light-sensitive color photographic material comprising at least one light-sensitive silver halide emulsion layer is developed with a color developer agent containing a primary aromatic amino group in the presence of a color coupler or color providing compound to form an image dye and in the presence of a thioether compound associated with the material and capable of releasing, on reaction with color developer oxidation products, a diffusible silver halide development inhibitor, wherein the improvement comprises said thioether compound is of the following formula I or of its tautomeric form I a:

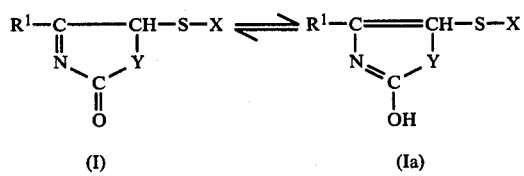

wherein
R¹ represents a hydrocarbyl group,
Y represents —S— or —NR²— wherein R² represents hydrogen, a hydrocarbyl group, a heterocyclic group attached through a ring carbon atom, or an electron-attracting substituent, selected from the group consisting of -CN, alkoxycarbonyl, carbamoyl, sulfamoyl, alkylsulfonyl, arylsulfonyl, an acyl group derived from an alkyl carbocyclic acid and aroyl, and
X represents an aliphatic group, an aromatic group, or a 5- or 6-membered heterocyclic aromatic group having at least one nitrogen atom such that when it is split off together with the sulfur atom of the thioether bridge, it forms a diffusible mercapto compound which inhibits development of the silver halide.

2. The process as claimed in claim 1, wherein R¹ represents a phenyl group.

3. The process as claimed in claim 1, wherein R¹ represents an alkyl group having from 1 to 18 C atoms.

4. Color photographic material comprising at least one light sensitive silver halide emulsion layer the material being such that reaction with the oxidation product of a primary aromatic amino silver halide developer forms an image and containing in said light sensitive layer or in a non-light-sensitive binder layer associated therewith at least one non-diffusing thioether compound capable of releasing, on reaction with color developer oxidation products, a diffusible silver halide development inhibitor, wherein the improvement comprises said thioether compound is of the following formula I or of its tautomeric form Ia:

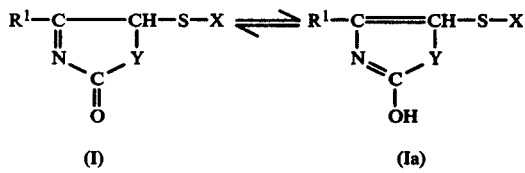

(I) (Ia)

wherein $R^1$ represents a hydrocarbyl group,

Y represents —S— or —$NR^2$— wherein $R^2$ represents hydrogen, a hydrocarbyl group, a heterocyclic group attached through a ring carbon atom, or an electron-attracting substituent, selected from the group consisting of -CN, alkoxycarbonyl, carbamoyl, sulfamoyl, alkylsulfonyl, arylsulfonyl, alkoyl and aroyl, and X represents an aliphatic group, an aromatic group of a 5- or 6-membered heterocyclic aromatic group such having at least at least one nitrogen atom that when it is split off together with the sulfur atom of the thioether bridge, it forms a dissusible mercapto compound which inhibits development of the silver halide at least one of $R^1$ and $R^2$ substituents containing a photographically inert group providing the thioether compound with a diffusion-fast property in a hydrocyclic colloid of the photographic material.

5. Material as claimed in claim 4, wherein $R^1$ represents a phenyl group.

6. Material as claimed in claim 4, wherein $R^1$ represents an alkyl group having from 1 to 18 C atoms.

7. Material as claimed in claim 4, wherein X represents a 5 membered or 6-membered heteroaromatic group having at least one nitrogen atom.

8. Material as claimed in claim 4, wherein a layer associated with the light-sensitive silver halide emulsion layer contains a non-diffusing color coupler or a non-diffusing color providing compound.

* * * * *